US008982443B2

(12) United States Patent
Yamada et al.

(10) Patent No.: US 8,982,443 B2
(45) Date of Patent: Mar. 17, 2015

(54) ORGANIC COMPOUND AND ELECTROCHROMIC DEVICE INCLUDING THE SAME

(75) Inventors: Kenji Yamada, Yokohama (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/807,060

(22) PCT Filed: Jun. 10, 2011

(86) PCT No.: PCT/JP2011/063988
§ 371 (c)(1),
(2), (4) Date: Dec. 27, 2012

(87) PCT Pub. No.: WO2012/002185
PCT Pub. Date: Jan. 5, 2012

(65) Prior Publication Data
US 2013/0100517 A1 Apr. 25, 2013

(30) Foreign Application Priority Data

Jun. 30, 2010 (JP) ................................. 2010-149481
Feb. 10, 2011 (JP) ................................. 2011-027540
Mar. 23, 2011 (JP) ................................. 2011-064398

(51) Int. Cl.
G02F 1/15 (2006.01)
C07D 495/14 (2006.01)
(Continued)

(52) U.S. Cl.
CPC ............. *C07D 495/14* (2013.01); *C07D 519/00* (2013.01); *G02F 1/15* (2013.01); *G02F 1/1521* (2013.01); *C09K 11/06* (2013.01); *C09K 2211/1092* (2013.01)
USPC ........................................................ 359/265

(58) Field of Classification Search
USPC ............. 359/245, 265–275; 257/40; 428/418; 523/404; 525/524
See application file for complete search history.

(56) References Cited

U.S. PATENT DOCUMENTS 7,746,533 B2 6/2010 Sotzing et al.
2002/0141032 A1 10/2002 Guarr
(Continued)

FOREIGN PATENT DOCUMENTS

CN 101432250 A 5/2009
CN 103124732 A 5/2013
(Continued)

OTHER PUBLICATIONS

Yanming Sun, Yongqiang Ma, et al., Advanced Functional Materials 2006, 16, pp. 426-432, "High-Performance and Stable Organic Thin-Film Transistors Based on Fused Thiophenes".
(Continued)

*Primary Examiner* — Mahidere Sahle
(74) *Attorney, Agent, or Firm* — Canon U.S.A., Inc. IP Division

(57) ABSTRACT

Provided is a novel electrochromic compound that is excellent in oxidation-reduction repetition and highly transparent when bleached and does not show optical absorption in the visible light region.
The compound is an organic compound represented by General Formula [1] shown in Claim 1.
In the General Formula [1], A and A' are each independently selected from hydrogen atoms, alkyl groups, alkoxy groups, and aryl groups, wherein at least one of A and A' is selected from the alkyl groups, the alkoxy groups, and the aryl groups. $R_1$ and $R_2$ independently represent a hydrogen atom, a halogen atom, an alkyl group, an alkoxy group, an aryl group, an aralkyl group, an amino group, or a silyl group; and n represents 1 or 2.

15 Claims, 4 Drawing Sheets

(51) Int. Cl.
*C07D 519/00* (2006.01)
*C09K 11/06* (2006.01)

(56) References Cited

U.S. PATENT DOCUMENTS

| | | | |
|---|---|---|---|
| 2007/0139756 A1* | 6/2007 | Agrawal et al. | 359/265 |
| 2012/0314272 A1 | 12/2012 | Yamada | |
| 2013/0190513 A1 | 7/2013 | Yamada et al. | |

FOREIGN PATENT DOCUMENTS

| | | | |
|---|---|---|---|
| JP | 51-146253 A | | 12/1976 |
| JP | 56-67881 A | | 6/1981 |
| JP | 2006-089413 A | | 4/2006 |
| JP | 2006-089413A A | | 4/2006 |
| JP | 2006089413 A | * | 4/2006 |
| JP | 2007-241238 A | | 9/2007 |
| JP | 2007-291013 A | | 11/2007 |
| JP | 2008-512727 A | | 4/2008 |
| JP | 2008-116665 A | | 5/2008 |
| JP | 2008-207170 A | | 9/2008 |
| JP | 2008-248249 A | | 10/2008 |
| JP | 2009-215333 A | | 9/2009 |
| JP | 2009-215333A A | | 9/2009 |
| JP | 2009215333 A | * | 9/2009 |
| JP | 2009-260287 A | | 11/2009 |
| JP | 2010-117409 A | | 5/2010 |
| WO | 2006/029344 A2 | | 3/2006 |
| WO | 2010/013532 A1 | | 2/2010 |
| WO | 2012/002185 A1 | | 1/2012 |

OTHER PUBLICATIONS

Zhang, et al., "Synthesis, Self-Assembly and Solution-Processed Field-Effect Transistors of a Liquid Crystalline Bis (dithienothiophene) Derivative", J. Phys. Chem. C, (2009), pp. 16232-16237, vol. 113.

Zhang, et al., "Effect of substituents on electronic properties, thin film structure and device performance of dithienothiophene-phenylene cooligomers", Thin Solid Films, (2009), pp. 2968-2973, vol. 517.

Wang, et al., Nanopatterning of Donor/Acceptor Hybrid Supramolecular Architectures on Highly Oriented Pyrolytic Graphite: A Scanning Tunneling Microscopy Study, J. Am. Chem. Soc., (2008), pp. 13433-13441, vol. 130.

Christian B. Nielsen et al. "Discrete Photopatternable [pi]—Conjugated Oligomers for Electrochromic Devices", Journal of the American Chemical Society, vol. 130, No. 30, Jul. 1, 2008, pp. 9734-9746, XP055142908.

* cited by examiner

ORGANIC COMPOUND AND ELECTROCHROMIC DEVICE INCLUDING THE SAME

TECHNICAL FIELD

The present invention relates to a novel organic compound and an electrochromic device including the same.

BACKGROUND ART

Various materials have been reported as electrochromic (hereinafter may be abbreviated as "EC") materials of which optical absorption properties (colored state and light transmittance) are changed by an electrochemical oxidation-reduction reaction. Metal oxides, such as $WO_3$, are known as inorganic EC materials, but they have a problem in that the method of forming a film thereof is limited to, for example, deposition, which prevents the film from being formed over a large area.

Organic EC materials are described in, for example, PTL 1 disclosing an EC device including an electrically conductive polymer and PTL 2 disclosing an EC device including an organic low-molecular-weight compound such as viologen.

The electrically conductive polymer described in PTL 1 can be directly formed as an EC layer on an electrode by electropolymerization of a monomer. As the electrically conductive polymer that forms the EC layer, for example, polythiophene, polyaniline, and polypyrrole are known. In such electrically conductive polymers, electrochemical oxidation or reduction thereof changes the π-conjugated chain length of the main chain, the electronic state of the highest occupied molecular orbital (HOMO), and the absorption wavelength. These electrically conductive polymers have π-conjugated systems and show absorptions in the visible light region in neutral states. Therefore, they have colors, and the absorption wavelengths shift to the longer wavelength side (infrared region side) by oxidation. The absorption in the visible light region disappears by the shift to the infrared region side, and thereby the EC device loses its color.

On the other hand, in the EC material of the viologen compound described in PTL 2, a dication is dissolved in a solution in a bleached state, and viologen is converted into a radical cation by a reduction reaction to be deposited on an electrode and have a color.

However, these organic EC materials are low in stability and may not be sufficiently bleached even in the bleached states.

In PTL 1, stability is increased by delocalizing the generally unstable radical cation in the molecule. However, the stability is insufficient, which causes a problem of causing deterioration of the material and decrease of the performance by repeating an oxidation-reduction reaction.

Furthermore, the electrically conductive polymer in the neutral state has an absorption band in visible light. Accordingly, if there is a portion in which the electrochemical reaction is insufficient, remnant occurs to make it difficult to obtain high transparency.

In the viologen EC compound of PTL 2, repetition of deposition and dissolution results in a deterioration phenomenon, which is thought to be caused by insolubilization due to irreversible crystallization or polymerization. This deterioration causes "remnant" in which transparency is not obtained even in the bleached state. In addition, the viologen EC compound generates an unstable radical cation when reduced and, thereby, has a problem of being unstable.

CITATION LIST

Patent Literature

PTL 1 Japanese Patent Laid-Open No. 56-67881
PTL 2 Japanese Patent Laid-Open No. 51-146253

SUMMARY OF INVENTION

Accordingly, the present invention provides an organic compound that is stable even in the radical cation state and against repetition of oxidation-reduction and that also has high transparency not having optical absorption in the visible light region in the bleached state. Furthermore, the present invention provides an EC device including the organic compound.

Accordingly, the present invention provides an organic compound represented by the following General Formula [1]:

[Chem. 1]

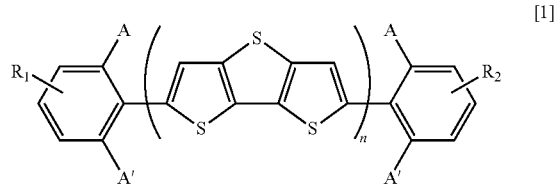

In General Formula [1], A and A' are each independently selected from the group consisting of hydrogen atoms, alkyl groups having 1 to 20 carbon atoms, alkoxy groups having 1 to 20 carbon atoms, and aryl groups; and at least one of A and A' is selected from the alkyl groups, the alkoxy groups, and the aryl groups.

The aryl groups may each have an alkyl group having 1 to 4 carbon atoms or an alkoxy group having 1 to 4 carbon atoms as a substituent.

$R_1$ and $R_2$ each independently represent a hydrogen atom, a halogen atom, an alkyl group having 1 to 20 carbon atoms, an alkoxy group having 1 to 20 carbon atoms, an aryl group, an aralkyl group, an amino group, or a silyl group; and n is 1 or 2.

The aryl group, the aralkyl group, the amino group, and the silyl group may each have an alkyl group having 1 to 4 carbon atoms as a substituent.

According to the present invention, it is possible to provide an organic compound having high stability against repetition of an oxidation-reduction reaction and discoloring in the electrically neutral state and thereby having high transparency not to cause remnant in the visible light region.

DESCRIPTION OF EMBODIMENTS

Figure 1:
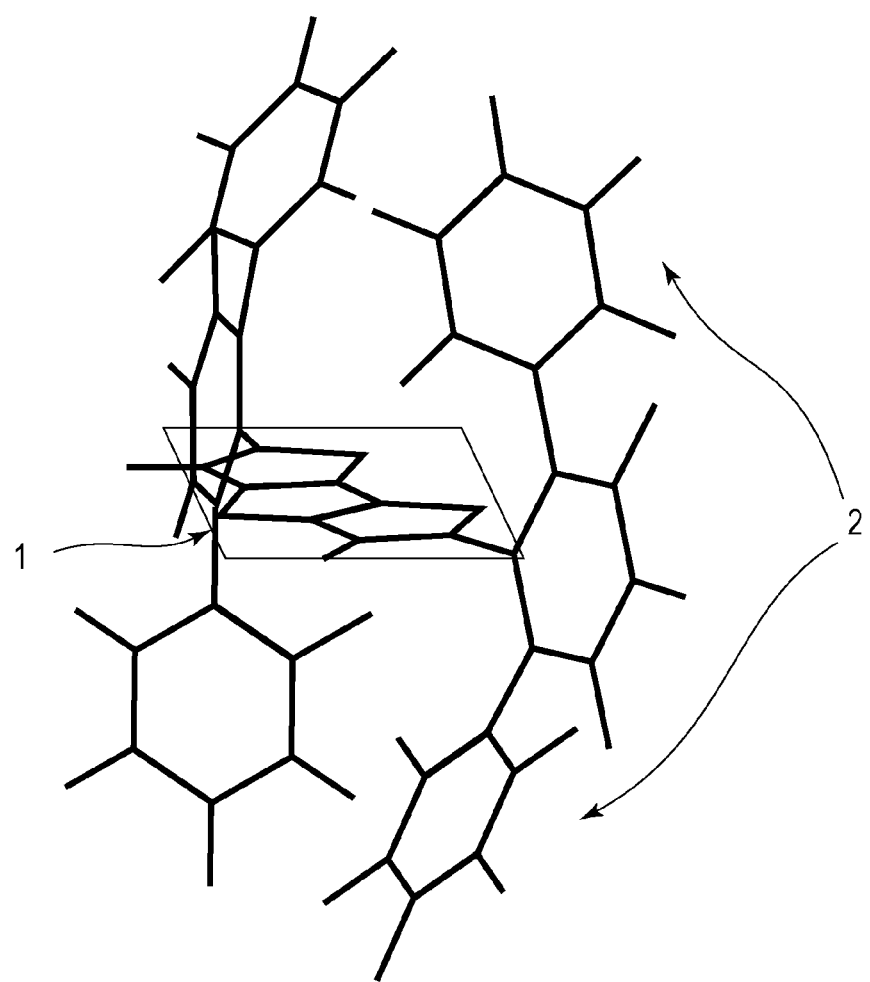
FIG. 1 is a diagram illustrating a molecular model of an example of the organic compound according to an embodiment.

The organic compound according to the present invention is represented by the following General Formula [1]:

[Chem. 2]

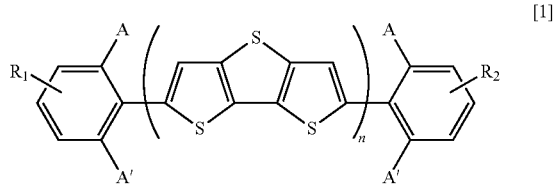

[1]

In General Formula [1], A and A' are each independently selected from hydrogen atoms, alkyl groups having 1 to 20 carbon atoms, aryl groups, and alkoxy groups, and at least one of A and A' is selected from the alkyl groups, the aryl groups, and the alkoxy groups.

The aryl groups may each have an alkyl group having 1 to 4 carbon atoms or an alkoxy group having 1 to 4 carbon atoms as a substituent.

$R_1$ and $R_2$ each independently represent a hydrogen atom, a halogen atom, an alkyl group having 1 to 20 carbon atoms, an alkoxy group having 1 to 20 carbon atoms, an aryl group, an aralkyl group, an amino group, or a silyl group; and n is 1 or 2.

The aryl group, the aralkyl group, the amino group, and the silyl group may each have an alkyl group having 1 to 4 carbon atoms as a substituent.

Examples of the alkyl group having 1 to 20 carbon atoms represented by A or A' include a methyl group, an ethyl group, an n-propyl group, an isopropyl group, an n-butyl group, a t-butyl group, a pentyl group, an octyl group, a dodecyl group, a cyclohexyl group, a bicyclooctyl group, and an adamanthyl group.

Examples of the alkoxy group represented by A or A' include a methoxy group, an ethoxy group, an isopropoxy group, an n-butoxy group, a t-butoxy group, an ethylhexyloxy group, an octyloxy group, and a decyloxy group.
Furthermore, the hydrogen atom in the alkyl group may be substituted with a fluorine atom into, for example, a trifluoromethyl group.

These alkyl groups can have a smaller number of the carbon atoms. From the viewpoint of easiness in synthesis, the alkyl group can be a methyl group, an ethyl group, an isopropyl group, or a t-butyl group, in particular, can be a methyl group, an ethyl group, or an isopropyl group.

Examples of the aryl group represented by A and A' include a phenyl group, a biphenyl group, a terphenyl group, a fluorenyl group, a naphthyl group, a fluoranthenyl group, an anthryl group, a phenanthryl group, a pyrenyl group, and a perylenyl group. From the viewpoint of easiness in synthesis, the aryl group can be a phenyl group or a biphenyl group.

Examples of the optional substituent of the aryl group include halogen atoms, alkyl groups having 1 to 20 carbon atoms, alkoxy groups, aryl groups, aralkyl groups, substituted amino groups, and substituted silyl groups. Specific examples of the alkyl group and the aryl group are the same as those of the alkyl group and the aryl group as the above-described substituents represented by A or A'. In the alkyl group, a hydrogen atom may be substituted with a fluorine atom.

At least one of A and A' is selected from the above-mentioned alkyl groups and the aryl groups. In order that A or A' exerts the effect of sterically protecting the dithienothiophene structure serving as the optical absorption portion of the core, the substituent represented by A or A' can be bulky. Specifically, the substituent can be a phenyl group, a biphenyl group, an isopropyl group, a t-butyl group, or a dodecyl group. The phenyl group and the biphenyl group may have an alkyl group as a substituent.

When one of A and A' is selected from the alkyl groups and the aryl groups, the other may be a hydrogen atom.

Examples of the alkyl group and the aryl group as the substituents represented by $R_1$ and $R_2$ are the same as those of the alkyl group and the aryl group as the above-described substituents represented by A or A'. Other examples of the substituents represented by $R_1$ and $R_2$ include alkoxy groups such as a methoxy group, an ethoxy group, an octyloxy group, and a decyloxy group; aralkyl groups such as a benzyl group and a phenylethyl group; substituted amino groups such as a dimethylamino group and a diphenylamino group; and substituted silyl groups such as a trimethylsilyl group and a triisopropylsilyl group.

Among these substituents, electron-donating substituents have an effect of increasing the electron density of the dithienothiophene portion of the core. The use of such a substituent decreases the oxidation potential through the electron donation to show an effect of reducing the driving voltage as an EC device. Accordingly, the substituent represented by $R_1$ or $R_2$ can be particularly a methyl group, an ethyl group, a methoxy group, or a dimethylamino group, which have high electron-donating properties.

Furthermore, these substituents represented by $R_1$ or $R_2$ can be introduced at the para-position of the phenyl group that binds to dithienothiophene, in order to inhibit side reactions, such as electropolymerization, accompanied by oxidation-reduction.

The organic compound according to the present invention is composed of a dithienothiophene structure of the core serving as an optical absorption portion and a structure in which phenyl groups having substituents at the ortho-positions are introduced at the 2-position and the 6-position of the dithienothiophene.

The dithienothiophene structure serving as the core of the structure of the organic compound according to the present invention is the optical absorption portion in the organic compound according to the present invention. This dithienothiophene structure has a structure in which three thiophene rings are condensed. A compound including one or two repeating dithienothiophene units (i.e., n represents 1 or 2) has a shorter π-conjugated system, compared with electrically conductive polymers. In this short π-conjugated system, the energy of absorbed light is high, and the light of high energy has a short wavelength.

Therefore, the organic compound according to the present invention in the neutral state has optical absorption in the ultraviolet region and does not have absorption in the visible light region and thereby shows high transparency.

In addition, the compound in the oxidized state has optical absorption in the visible light region, being in the colored state. On the other hand, since electrically conductive polymers have optical absorption in the visible light region in the neutral state, "remnant", an absorption band in the visible light region, occurs in a portion where the electrochemical reaction is insufficient even in the oxidized state. In contrast, the compound according to the present invention can maintain high transparency not having an absorption band in the visible light region even if a portion where the electrochemical reaction is insufficient is present.

Dithienothiophene has high molecular planarity. This has an effect by the resonance structure of enhancing the stability of the radical cation, which is generated in the oxidized state.

However, the stability of the radical cation of dithienothiophene is insufficient.

Accordingly, in the compound according to the present invention, phenyl groups having substituents at the ortho-positions are introduced at the 2-position and the 6-position of the dithienothiophene.

The compound is characterized by having an effect of protecting the dithienothiophene skeleton that generates a radical cation by steric hindrance of the introduced bulky phenyl groups having substituents at the ortho-positions.

In general, the instability of radical cations is caused by, for example, recombination between radicals due to high reactivity of the radicals or hydrogen abstraction from another molecule by the radical. That is, the instability is caused by a reaction of a radical due to a contact of the radical with another molecule.

Therefore, the steric hindrance of the phenyl groups having substituents at the ortho-positions and binding to the dithienothiophene has a high effect of enhancing stability of the radical cation. This is because the steric hindrance groups inhibit the dithienothiophene from being in contact with other molecules.

For example, the phenyl groups having substituents at the ortho-positions are present on a plane orthogonal to the plane that is formed by the dithienothiophene skeleton. Accordingly, the bulky phenyl groups having substituents at the ortho-positions function as steric hindrance showing an effect of inhibiting the dithienothiophene skeleton from being in contact with other molecules (cage effect).

FIG. 1 shows a steric structure of a molecule when A and A' of the organic compound according to the present invention are phenyl groups. The reference numeral 1 designates a dithienothiophene skeleton, and the reference numeral 2 designates a phenyl group.

In this structure, the dithienothiophene skeleton serving as the core is prevented from coming into intermolecular contacts with other molecules by the phenyl groups as A and A'.

Furthermore, the structure of each phenyl group portion (cage portion) having the steric hindrance groups A and A' plays a role of protecting the oxidation coloring portion (core portion) from attack by other substrates present as, for example, another electrochromic material molecule or an impurity. Therefore, the cage portion can have a molecular shape of covering the core portion.

Accordingly, the substituents introduced into the phenyl groups can be more bulky and can have a ring structure rather than a methyl group.

The cage portion and the core portion can have less electronic resonance structures. In a structure having a n-electron system such as an aromatic ring at the cage portion, bleeding of highest occupied molecular orbital (HOMO) locally present in the core portion to the cage portion can be decreased by reducing the electronic resonance effects of the cage portion and the core portion. In actual molecules, the molecular orbital cannot be completely interrupted due to quantum-chemical fluctuation. However, since resonance does not occur when the n-electron orbitals of the cage portion and the core portion are orthogonal to each other, the phenyl group serving as the cage portion connected to the core portion can be orthogonal to the molecular plane of the core portion. In this viewpoint, both ortho-positions, rather than only one ortho-position, of the phenyl group can be substituted with substituents.

In order to achieve this cage effect, a cage portion can have an oxidation potential relatively higher than that of the core portion and have a structure to be hardly oxidized. It is conceivable that in such a configuration, the radical cation in oxidation is localized in the core portion to block attack from the outside of the molecule, resulting in a remarkable improvement in stability of the radical cationic state.

Since the radical cation generated in the core portion can be stabilized by increasing the electron density of the core portion, the substituents A and A' of the phenyl group in the cage portion can be those having electron-donating properties. Examples of the substituent having a high electron-donating property and high steric hindrance include an isopropoxy group, a t-butoxy group, and an ethylhexyloxy group.

Specific structural formulae of the compounds according to the present invention are exemplified below, but the compounds according to the present invention are not limited thereto.

[Chem. 3]

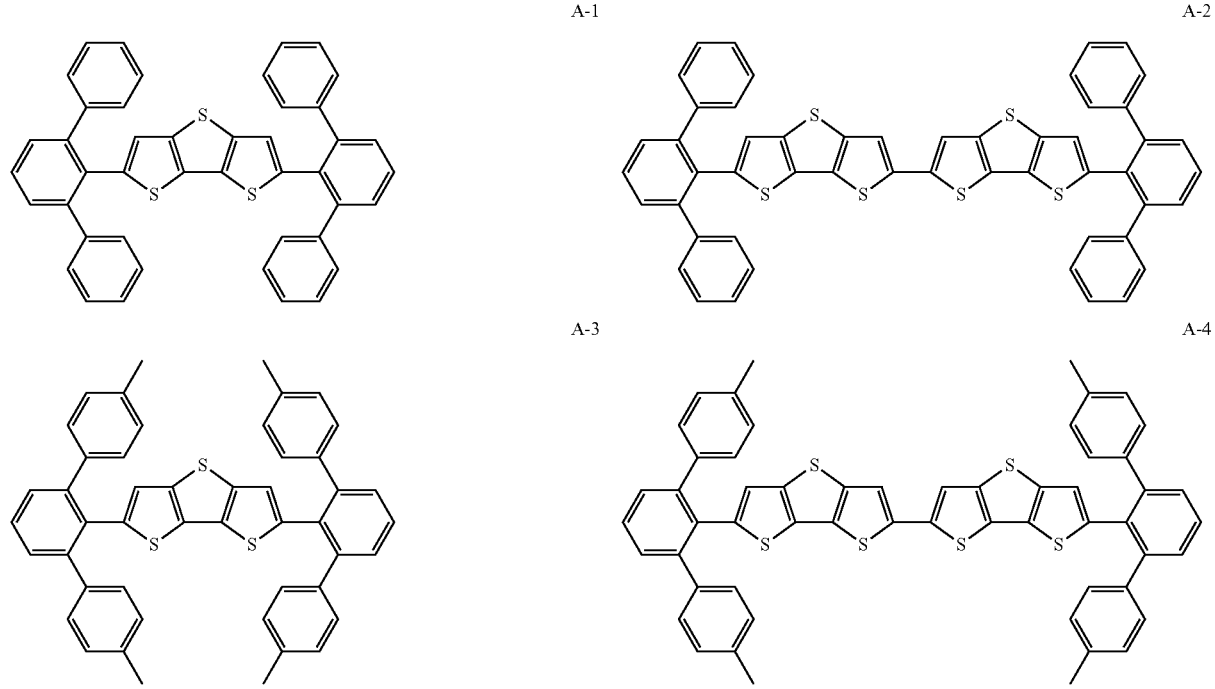

-continued
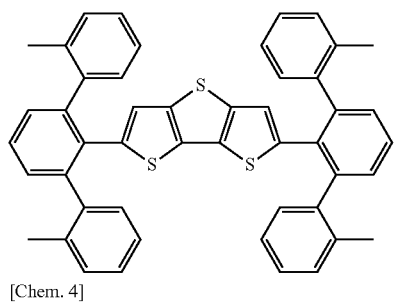
A-5
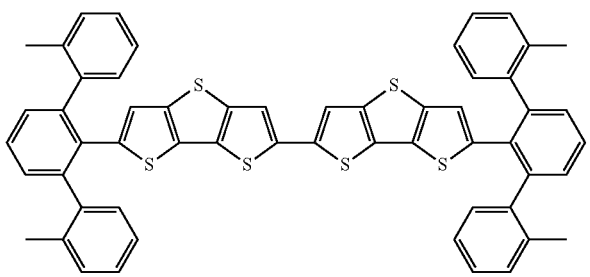
A-6
[Chem. 4]
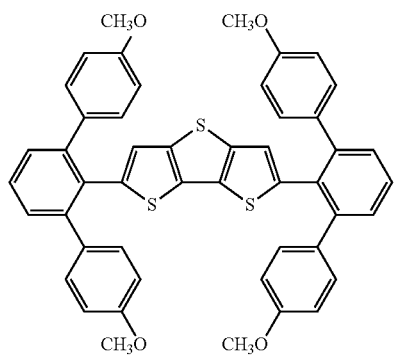
A-7
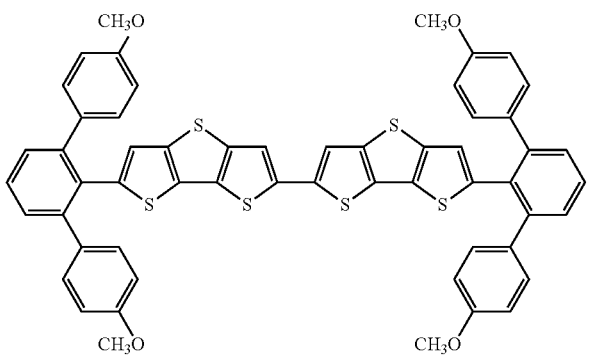
A-8
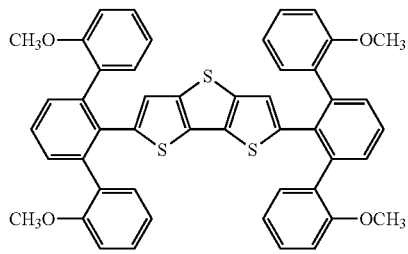
A-9
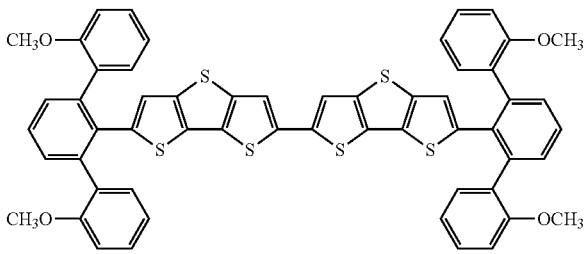
A-10
[Chem. 5]
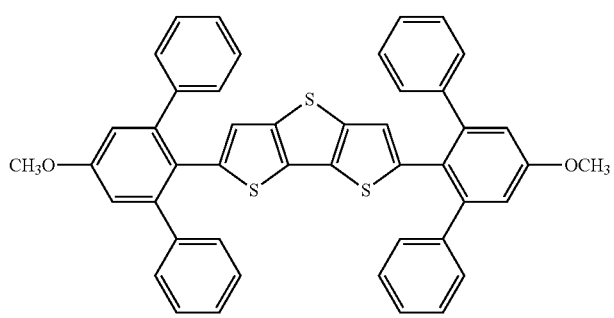
A-11
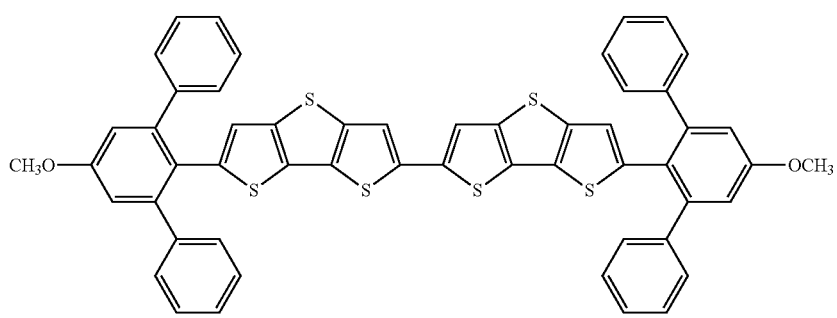
A-12

-continued
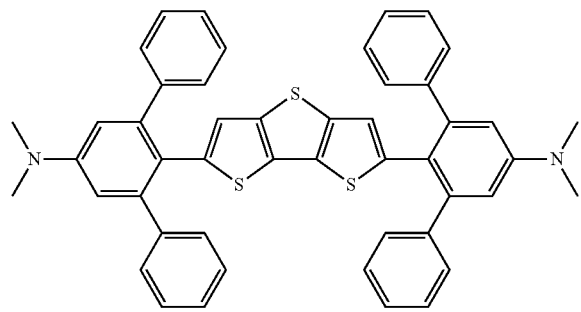
A-13
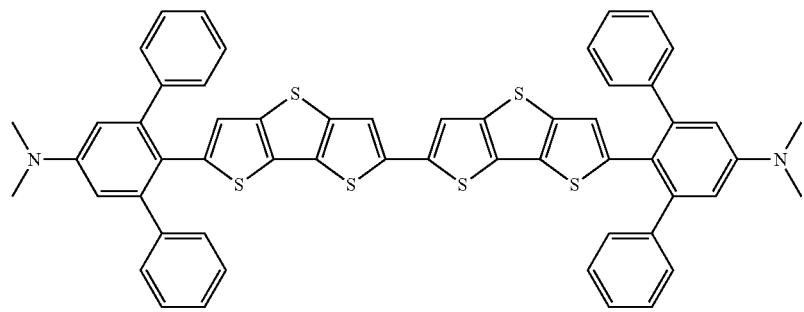
A-14
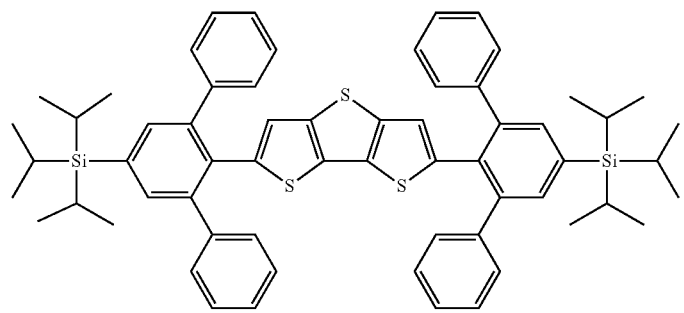
A-15
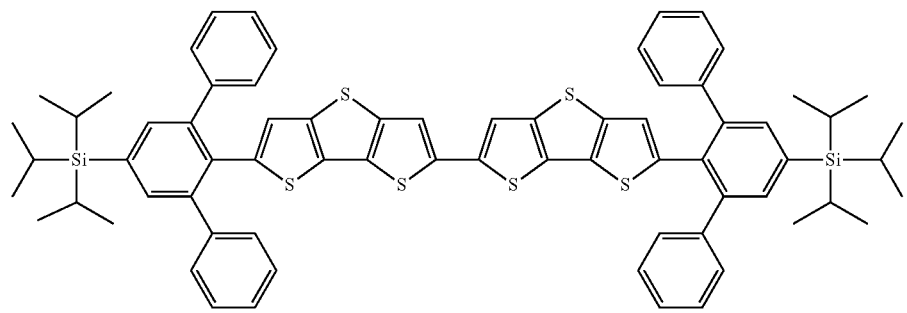
A-16
[Chem. 6]
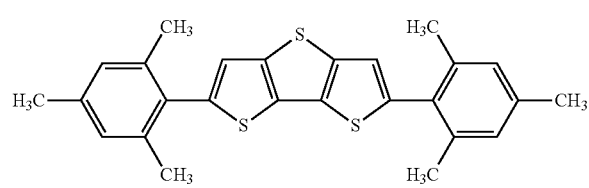
A-17

-continued
A-18
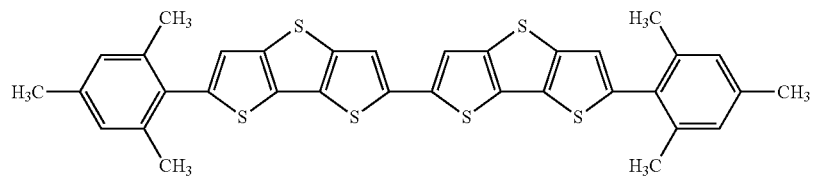
A-19
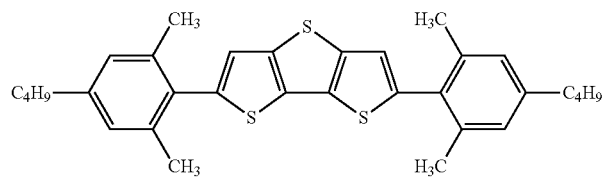
A-20
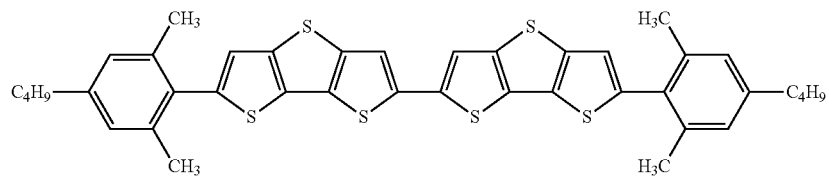
A-21
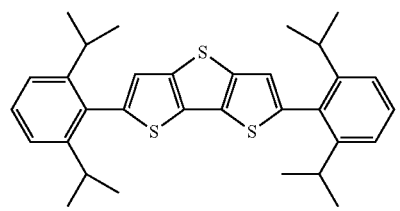
A-22
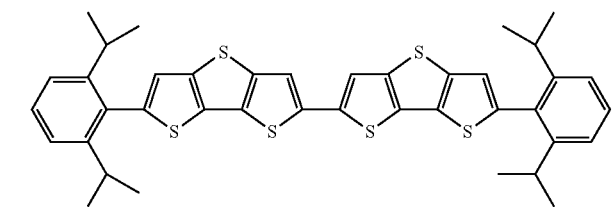
A-23
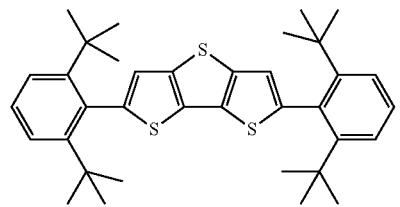
A-24
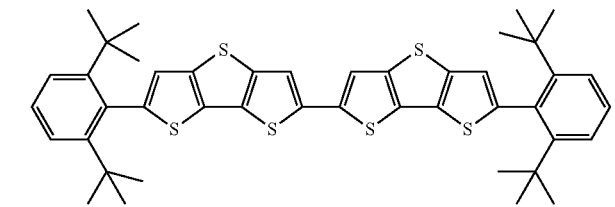
A-25
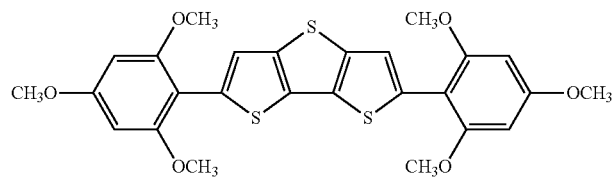
A-26
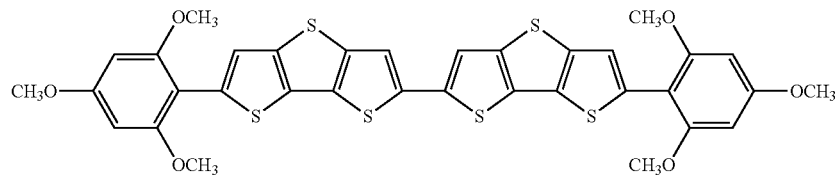
[Chem. 7]
B-1
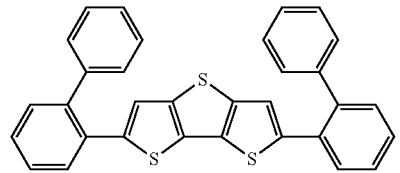
B-2
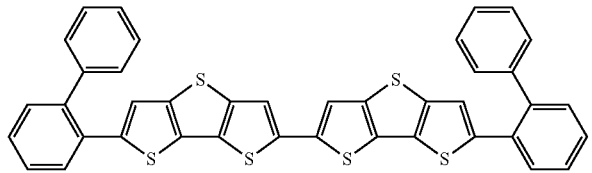

-continued
B-3
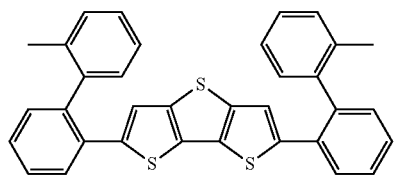
B-4
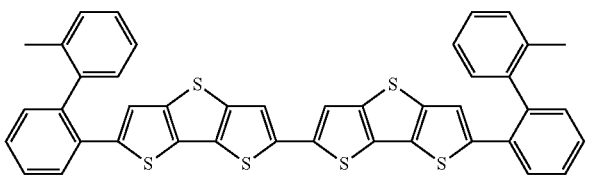
B-5
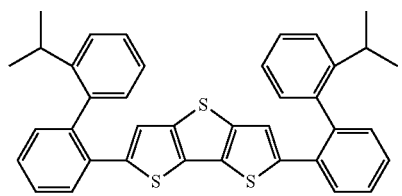
B-6
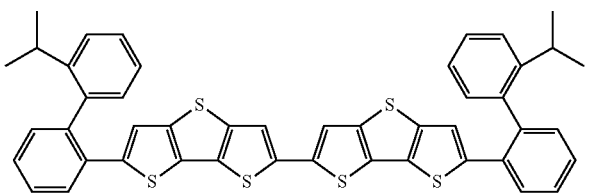
B-7
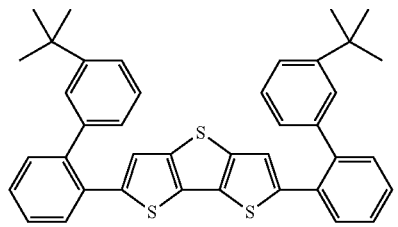
B-8
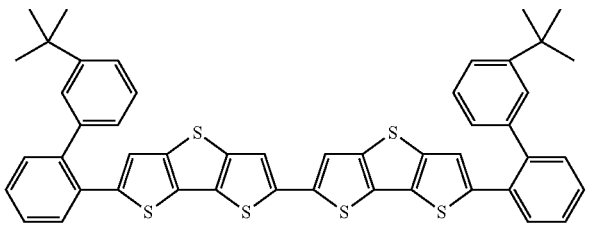
[Chem. 8]
B-9
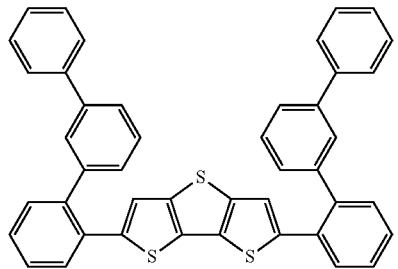
B-10
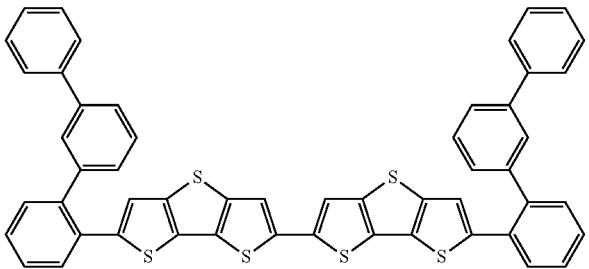
B-11
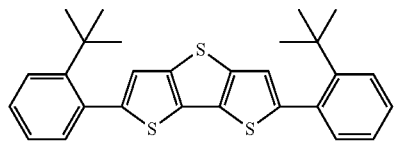
B-12
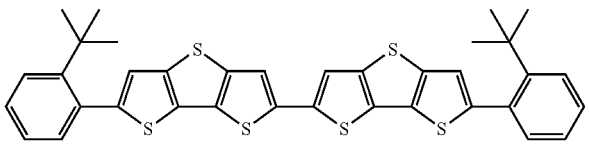
B-13
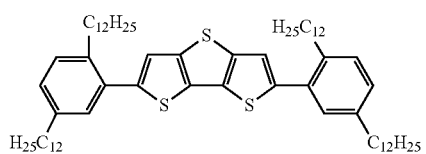
B-14
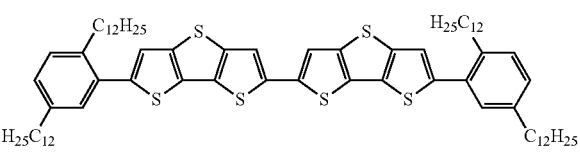

Among the exemplified compounds, in the compounds shown in the group A, A and A' in General Formula [1] are identical alkyl groups or aryl groups. The structures represented by these A and A' are present at the ortho-positions of the substituted phenyl group and thereby function as a skeleton to protect the dithienothiophene structure of the core by the steric hindrance. Accordingly, an EC device including such a compound as an EC material has high durability against repetition of an oxidation-reduction reaction.

Among the exemplified compounds, in the compounds shown in the group B, one of A and A' in General Formula [1] is a hydrogen atom, and the other is an alkyl group or an aryl group. In these compounds, since the alkyl group or the aryl group has a bulky structure or a long alkyl chain, only one of the substituents A and A' can protect the dithienothiophene structure of the core.

Among the compounds shown in the group A, in particular, the compounds represented by the following General Formula [2] can be used.

[Chem. 9]

[2]

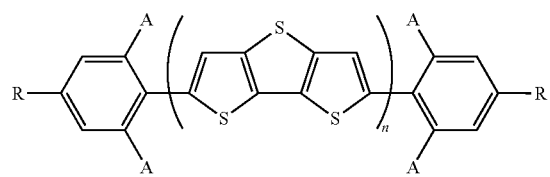

In General Formula [2], all 'A's represent identical substituents and are methyl groups or phenyl groups; and both 'R's represent identical substituents and are selected from hydrogen atoms and alkyl groups having 1 to 4 carbon atoms.

The phenyl groups may each have an alkyl group having 1 to 4 carbon atoms as a substituent, and n is 1 or 2.

The compound according to the present invention can be synthesized using the reaction shown by the Formulae [3] below. In the formulae, X represents a halogen atom. The compound can be synthesized by a coupling reaction, catalyzed by a Pd catalyst, of a combination of a halogenated dithienothiophene and a boronic acid or boronic ester compound of a phenyl group having substituents at the ortho-positions or a combination of a boronic acid or boronic ester compound of dithienothiophene and a halogenated phenyl group having substituents at the ortho-positions.

[Chem. 10]

[3]

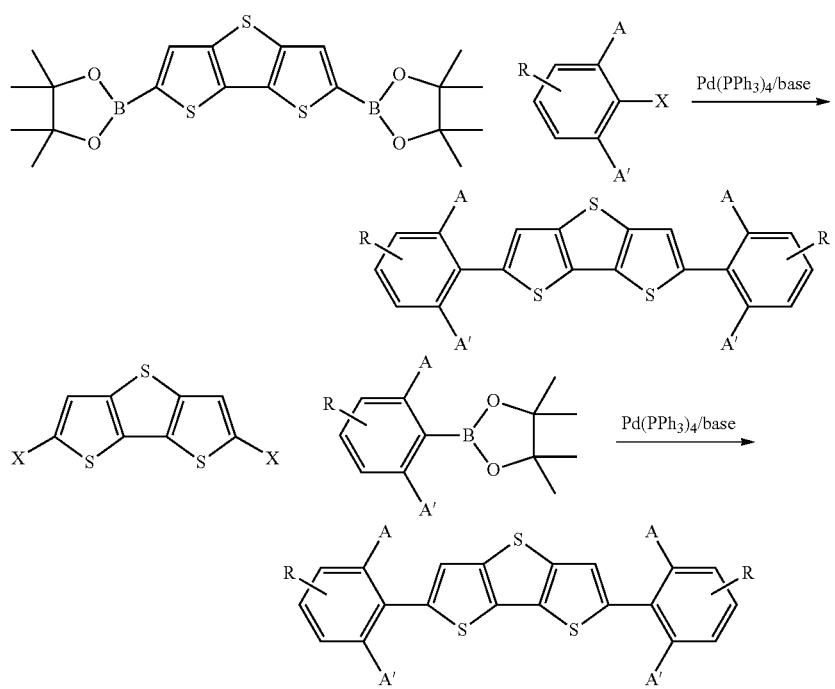

The EC device according to an embodiment will be described.

A first aspect of the electrochromic device according to the embodiment is a device including a pair of electrodes and an electrochromic layer and an ion conductive layer that are disposed between the pair of electrodes. This electrochromic layer includes the organic compound according to the present invention.

The EC device according to the embodiment can be obtained by forming a film of the organic compound according to the present invention on an electrode substrate. The method of forming the film is not particularly limited, but a thin film can be formed by a known method, for example, by dissolving the compound in an appropriate solvent and applying it by a known coating method (e.g., spin coating, dipping, casting, an LB method, or an ink-jetting method), vacuum deposition, ionized vapor deposition, sputtering, or plasma coating.

The solvent that is used in the solution for a coating method is not particularly limited as long as it can dissolve the EC compound and can be removed by volatilization after application, and examples thereof include dimethyl sulfoxide, dimethylacetamide, dimethyl formamide, N-methylpyrrolidone, propylene glycol methylether acetate, dimethoxyethane, acetonitrile, propionitrile, tetrahydrofuran, dioxane, methanol, ethanol, propanol, chloroform, toluene, xylene, methyl ethyl ketone, and cyclohexanone.

The ion conductive material used in the ion conductive layer is not particularly limited as long as it is an ion-dissociative salt that has good solubility in a solution or high compatibility to a solid electrolyte and contains an anion having an electron-donating property being enough for coloring the EC compound. For example, a liquid ion conductive material, a gelatinized-liquid ion conductive material, or a solid ion conductive material can be used.

The liquid ion conductive material can be one in which a supporting electrolyte such as a salt, an acid, or an alkali is dissolved in a solvent. The solvent is not particularly limited as long as it can dissolve the supporting electrolyte, but one having polarity can be particularly used. Specific examples thereof include water and organic polar solvents such as methanol, ethanol, propylene carbonate, ethylene carbonate, dimethyl sulfoxide, dimethoxyethane, acetonitrile, γ-butyrolactone, γ-valerolactone, sulfolane, dimethyl formamide, dimethoxyethane, tetrahydrofuran, propionitrile, dimethylacetamide, methylpyrrolidinone, and dioxolane.

The salt as the supporting electrolyte is not particularly limited, and inorganic ionic salts such as various alkali metal salts and alkaline earth metal salts, quaternary ammonium salts, and cyclic quaternary ammonium salts can be exemplified. Specific examples include alkali metal salts of Li, Na, and K such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, $KSCN$, and $KCl$; and quaternary ammonium salts and cyclic quaternary ammonium salts such as $(CH_3)_4NBF_4$, $(C_2H_5)_4NBF_4$, $(n-C_4H_9)_4NBF_4$, $(C_2H_5)_4NBr$, $(C_2H_5)_4NClO_4$, and $(n-C_4H_9)_4NClO_4$.

As the gelatinized-liquid ion conductive material, for example, those including the above-mentioned liquid ion conductive material and also a polymer or a gelling agent for increasing the viscosity or for gelation can be used. The polymer (gelling agent) is not particularly limited, and examples thereof include polyacrylonitrile, carboxymethyl cellulose, polyvinyl chloride, polyethylene oxide, polypropylene oxide, polyurethane, polyacrylate, polymethacrylate, polyamide, polyacrylamide, polyester, and Nafion (registered trademark).

The solid ion conductive material is not particularly limited as long as it is a solid at room temperature and has ion conductivity, and examples thereof include polyethylene oxide, polymers of oxyethylene methacrylate, Nafion (registered trademark), and polystyrene sulfonate.

These ion conductive materials may be used alone or in a combination of two or more thereof.

Examples of the electrode material include metals and metal oxides such as indium tin oxide (ITO) alloys, tin oxide (NESA), indium zinc oxide (IZO), silver oxide, vanadium oxide, molybdenum oxide, gold, silver, platinum, copper, indium, and chromium; silicon materials such as polycrystalline silicon and amorphous silicon; and carbon materials such as carbon black, graphite, and glassy carbon. Furthermore, electrically conductive polymers (e.g., polyaniline, polypyrrole, polythiophene, polyacetylene, polyparaphenylene, and polyethylene dioxythiophene (PEDOT)-polystyrene sulfonate complexes), the electrical conductivity of which is increased by, for example, doping, can be also used.

In an optical filter according to the embodiment, transparency as an optical filter is also required. Accordingly, those not showing light absorption in the visible light region: ITO, IZO, NESA, and electrically conductive polymers having enhanced electrical conductivity, can be particularly used. These can be used in various forms such as a bulk form or a fine particle form. These electrode materials may be used alone or in a combination of two or more thereof.

The method of forming the electrochromic device according to the embodiment is not particularly limited, and the device may be formed by a method in which a film as an EC layer is formed on an electrode substrate, and an ion conductive material is injected into the gap formed between the substrate and a sealed counter electrode substrate by vacuum injection, air injection, or a meniscus method; a method in which an ion conductive material layer is formed on an electrode substrate or on an electrode substrate on which a film as an EC layer is formed, and the substrate is attached to a counter electrode substrate; or a method in which an ion conductive material is used in a film-like form.

A second aspect of the electrochromic device according to the embodiment is a device including a pair of electrodes and a solution layer serving as the electrochromic layer and the ion conductive layer disposed between the pair of electrodes.

The solution layer in this case is not particularly limited as long as the electrochromic material and the supporting electrolyte can be dissolved therein, and those having polarity (high dielectric constant) can be particularly used.

Specific examples include water and organic polar solvent such as methanol, ethanol, propylene carbonate, ethylene carbonate, dimethyl sulfoxide, dimethoxyethane, acetonitrile, γ-butyrolactone, γ-valerolactone, sulfolane, dimethyl formamide, dimethoxyethane, tetrahydrofuran, propionitrile, benzonitrile, dimethylacetamide, methylpyrrolidinone, and dioxolane.

The electrochromic device according to the embodiment has excellent durability and high transparency when discolored and, thereby, can be suitably used for controlling quantity of incident light to an image pickup element such as a camera or controlling incident wavelength distribution characteristics. The control of incident wavelength distribution is effective for color temperature conversion in image pickup.

That is, the light quantity to be received by an image pickup device or incident wavelength distribution characteristics can be controlled by installing the EC device in an optical path of an optical system (lens system) communicating with an image pickup device. Since the EC device in the bleached state can show high transparency, transmitted light in a sufficient quantity relative to the incident light can be obtained. In the colored state, optical characteristics in which incident light is reliably shielded and modulated can be obtained. In addition, excellent oxidation-reduction repeating characteristics and a long operating life can be achieved.

EXAMPLES

Example 1

Synthesis of Exemplary Compound A-2

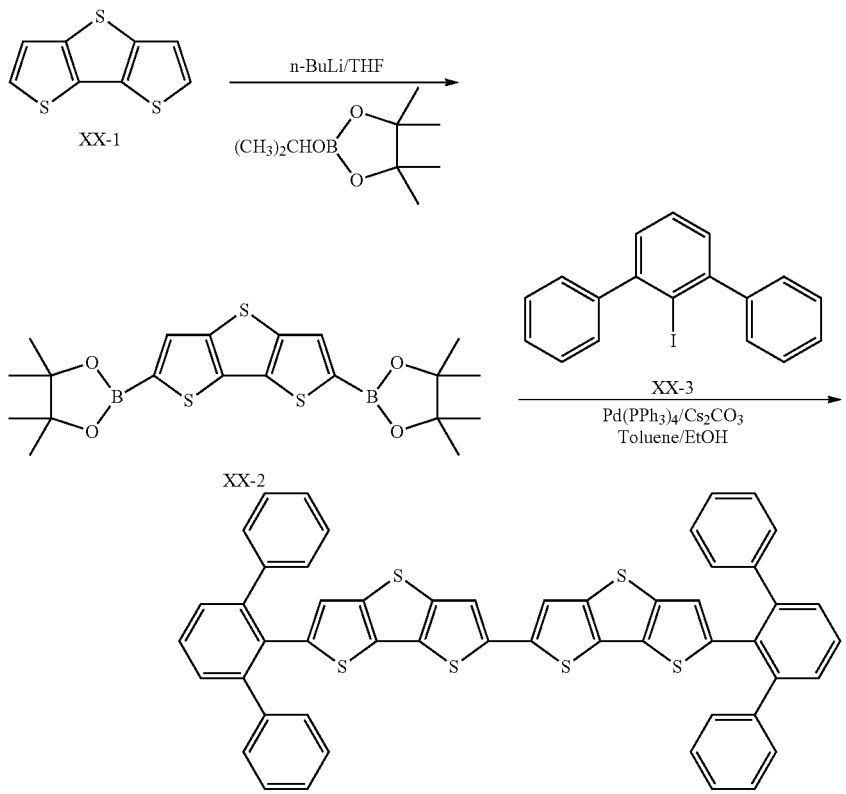

[Chem. 11]

(1) In a 50-mL reaction container, XX-1 (dithieno[3,2-b:2',3'-d]thiophene, 300 mg, 1.53 mmol) was dissolved in tetrahydrofuran (15 mL), followed by cooling to −78° C. Then, under a nitrogen atmosphere, a hexane solution of 2.5 M n-butyllithium (1.2 mL, 3.06 mmol) was dropwise added thereto. The reaction solution was maintained at −78° C. for 1 hour. Then, 2-isopropoxy-4,4,5,5-tetramethyl-1,3,2-dioxaborolane (1.56 mL, 7.65 mmol) was added to the reaction solution. After 30 minutes, the reaction solution was cooled to room temperature, followed by stirring at room temperature for 16 hours. A small amount of water was added to the solution to quench the reaction. After extraction with diethyl ether and washing with water, the ether layer was concentrated under reduced pressure to give a crude product, which was subjected to silica gel chromatography (mobile phase: hexane/ethyl acetate=1/1) for isolation and purification to obtain XX-2 (155 mg, yield: 23%) as a white solid powder.

(2) In a 50-mL reaction container, XX-2 (109 mg, 0.243 mmol) and XX-3 (190.4 mg, 0.535 mmol) were mixed in a toluene/ethyl alcohol (3 mL/1.5 mL) mixture solvent, and dissolved oxygen was removed by nitrogen. Note that XX-3 is a compound synthesized in accordance with the procedure described in The Journal of Organic Chemistry, 51, 3162 (1986). Then, Pd(PPh$_3$)$_4$ (14.0 mg, 0.01215 mmol) and an aqueous solution of 2 M cesium carbonate (1.5 mL) were added to the mixture under a nitrogen atmosphere, followed by heating to 85° C. and reaction at the temperature for 12 hours. The reaction solution was cooled to room temperature, concentrated under reduced pressure, and subjected to silica gel chromatography (mobile phase: hexane/toluene=3/1) for isolation and purification to obtain A-2 (35 mg, yield: 17%) as a white solid powder.

Mass-spectrometry (MS) and nuclear magnetic resonance spectrometry (NMR) of compound A-2 gave the results that the molecular weight and the ratio of integrated values of NMR peaks well agreed with the structure of compound A-2. Specifically, 846 as M$^+$ of this compound was confirmed by matrix-assisted laser desorption-ionization mass spectrometry (MALDI-MS). The measurement results of nuclear magnetic resonance spectrometry are shown below:

$^1$H-NMR (THF-d$_8$) σ (ppm): 7.52 (t, 2H), 7.42 (d, 4H), 7.38 (d, 2H), 7.25 (m, 8H), 7.19-7.11 (m, 12H), 6.70 (s, 2H).

$^{13}$C-NMR (THF-d$_8$) σ (ppm): 142.31, 140.43, 139.64, 139.51, 139.24, 130.03, 129.25, 128.29, 127.93, 127.16, 126.39, 125.24, 124.45, 121.91, 119.25.

Figure 2:
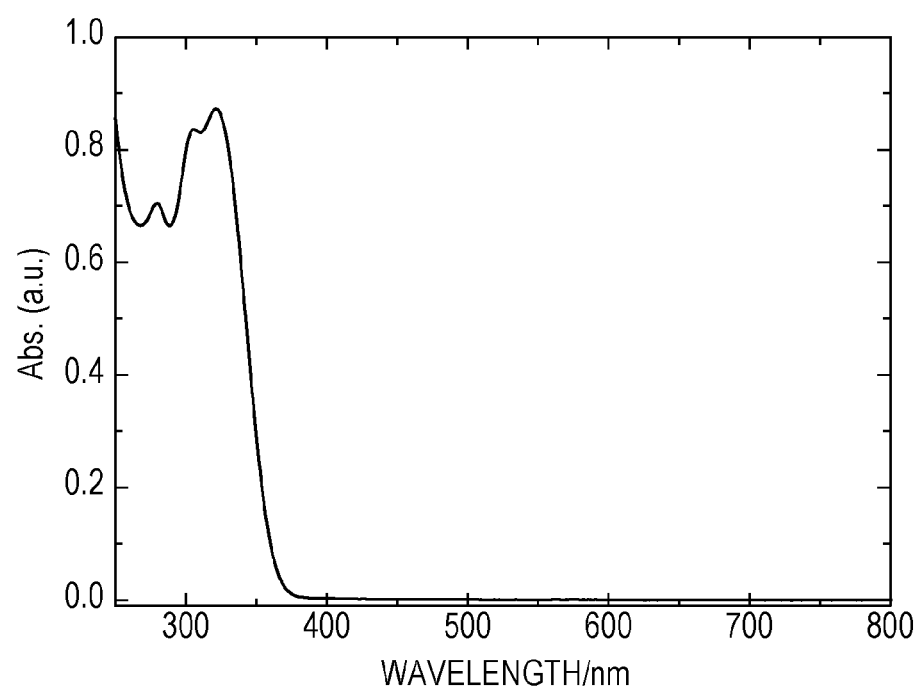
FIG. 2 is a diagram showing an ultraviolet and visible absorption spectrum of exemplary compound A-2.

The obtained exemplary compound A-2 was dissolved in chloroform, and the absorption spectrum of this solution obtained by measurement with an ultraviolet and visible spectrophotometer (V-560, manufactured by JASCO Corp.) is shown in FIG. 2.

The maximum absorption peak, λmax, was observed at 321.5 nm in the ultraviolet region. Since exemplary compound A-2 did not have absorption over the entire visible light region, it was a transparent material.

Example 2

Synthesis of Exemplary Compound A-17

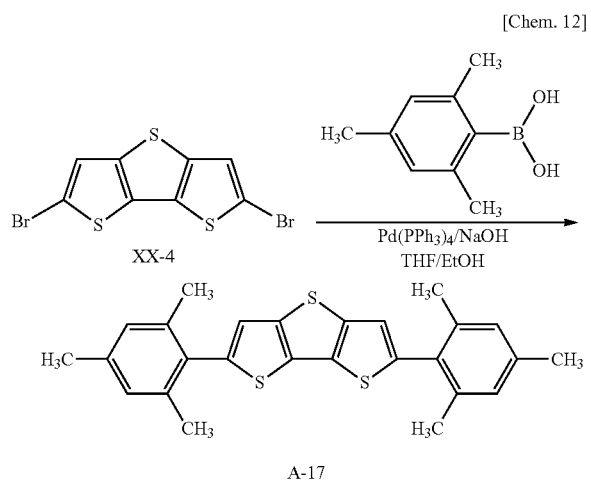

In a 50-mL reaction container, XX-4 (2,6-dibromodithieno[3,2-b:2',3'-d]thiophene, 200 mg, 0.565 mmol) and 2,4,6-trimethylphenylboronic acid (232 mg, 1.413 mmol) were mixed in a tetrahydrofuran/ethyl alcohol (8 mL/4 mL) mixture solvent, and dissolved oxygen was removed by nitrogen. Then, Pd(PPh$_3$)$_4$ (32 mg, 0.0285 mmol) and an aqueous solution of 2 M sodium hydroxide (4 mL) were added to the mixture under a nitrogen atmosphere, followed by heating to 80° C. and reaction at the temperature for 12 hours. The reaction solution was cooled to room temperature, concentrated under reduced pressure, and subjected to silica gel chromatography (mobile phase: hexane) for isolation and purification to obtain A-17 (28 mg, yield: 12%) as a white solid powder.

The structure of compound A-17 was confirmed by mass-spectrometry (MS) and nuclear magnetic resonance spectrometry (NMR). Specifically, 433 as M$^+$ of this compound was confirmed by matrix-assisted laser desorption-ionization mass spectrometry (MALDI-MS). The measurement results of nuclear magnetic resonance spectrometry are shown below:

$^1$H-NMR (CDCl$_3$) σ (ppm): 7.02 (s, 2H), 6.98 (s, 4H), 2.35 (s, 6H), 2.21 (s, 12H).

$^{13}$C-NMR (CDCl$_3$) σ (ppm): 142.02, 140.04, 138.58, 138.51, 131.20, 130.88, 128.19, 120.01, 29.73, 20.78.

The obtained exemplary compound A-17 was dissolved in chloroform, and the absorption spectrum of this solution was measured with an ultraviolet and visible spectrophotometer as in Example 1. The maximum absorption peak, λmax, was observed at 307.7 nm in the ultraviolet region, and no absorption was observed over the entire visible light region. Thus, it was shown that the compound A-17 was a transparent material.

Example 3 and Comparative Example 1

Stability in Oxidation-Reduction Cycle

Figure 3:
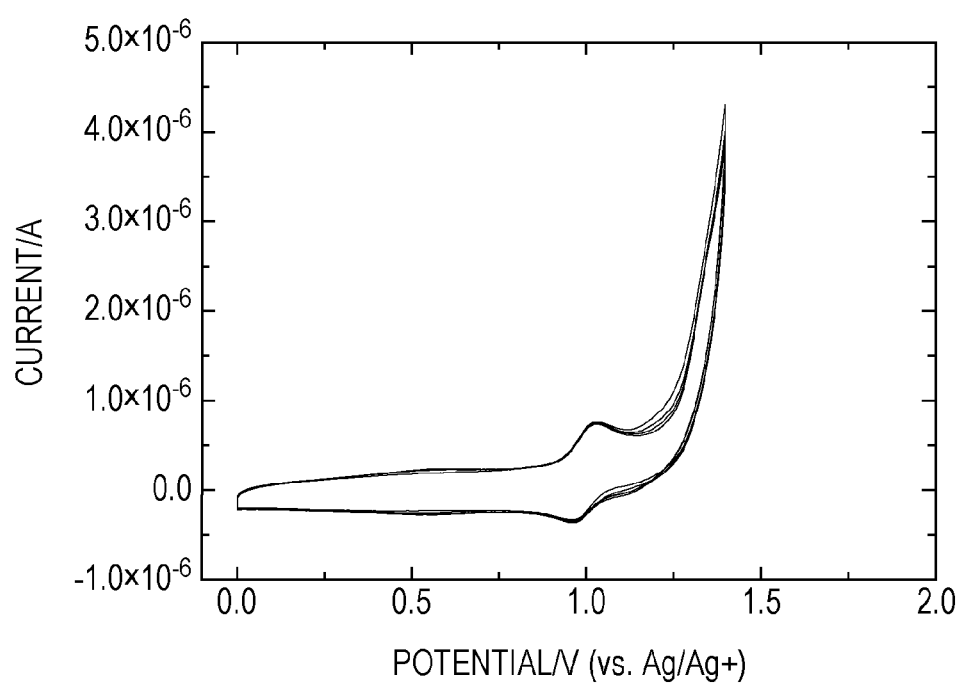
FIG. 3 is a diagram showing a cyclic voltammogram of exemplary compound A-17.

Compound A-2 obtained in Example 1 and compound A-17 obtained in Example 2 and, as a comparative compound, dithieno[3,2-b:2',3'-d]thiophene (DTT) not having bulky substituents were subjected to cyclic voltammetry (CV) measurement. The measurement was performed using a working electrode of glassy carbon, a counter electrode of platinum, and a reference electrode of silver, dissolving A-17 at a concentration of 1.0×10$^{-4}$ mol/L in a dichloromethane solution of tetrabutylammonium perchlorate (0.1 mol/L) serving as a supporting electrolyte, and at a sweep rate of 20 mV/s. Similarly, CV measurement was performed using A-2 or DTT as the compound to be dissolved. The CV measurement results of exemplary compound A-17 and comparative compound DTT are shown in FIGS. 3 and 4, respectively.

In the case of exemplary compound A-17 (FIG. 3), the CV curve was not changed even if the sweeping was repeated to show a reversible oxidation-reduction cycle. This means that the compound is very stable against repetition of oxidation-reduction. In this CV measurement of exemplary compound A-17, the compound was colored to yellow-green with oxidation and returned to be colorless and transparent by reduction, and thus electrochromic characteristics upon oxidation-reduction were confirmed. The change accompanied by this oxidation-reduction was measured with an ultraviolet and visible spectrophotometer. As shown in Example 2, the results were that the absorption peak λmax in the neutral state was at 307.7 nm, but in the acidic state, another absorption peak (λmax=430.0 nm) appeared, and this oxidation absorption peak disappeared with reduction to return the absorption spectrum in the original neutral state. Thus, reversible oxidation-reduction characteristics were shown.

Similarly, the CV curve of exemplary compound A-2 was not changed even if sweeping was repeated as in A-17, and it was confirmed that the reversible oxidation-reduction cycle was shown.

Figure 4:
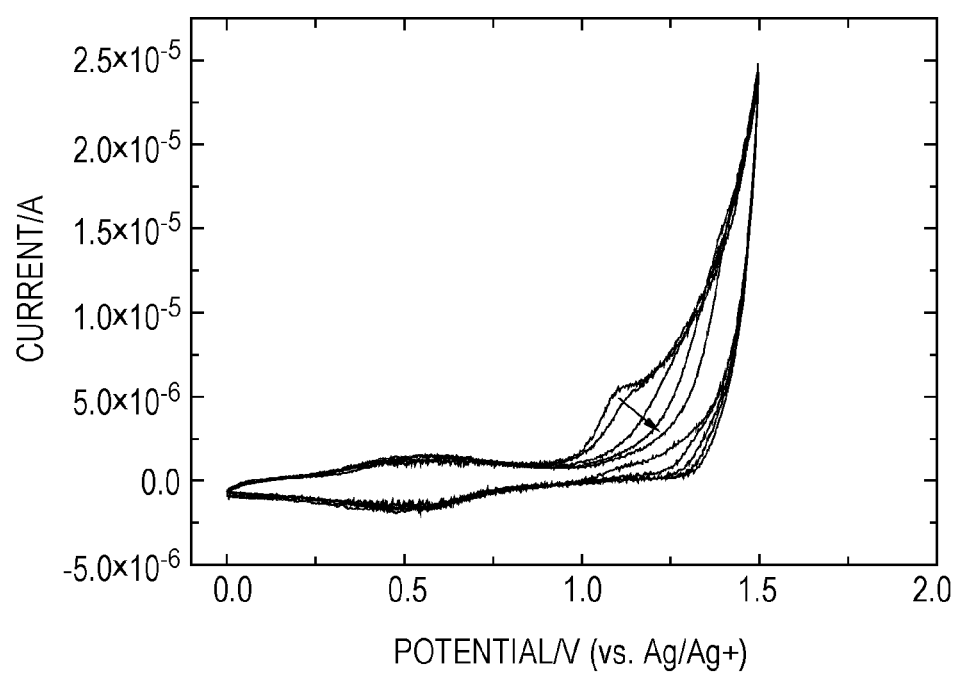
FIG. 4 is a diagram showing a cyclic voltammogram of dithienothiophene.

On the other hand, as shown in FIG. 4, in the case of comparative compound DTT, the oxidation peak near 1.15 V (vs. Ag/Ag+) shifted to the direction indicated by the arrow with an increase in the number of cycles of the sweeping. Thus, instability caused by repeating oxidation-reduction was shown.

It is assumed that these results showing excellent oxidation-reduction repeating characteristics of the compounds of the present invention are caused by that the DTT portions of exemplary compounds A-2 and A-17 of the present invention are sterically protected by the bulky terphenyl group or mesityl group, compared to the case of comparative compound DTT, and a side reaction or a deterioration reaction due to the radical cation generated by oxidation of DTT is inhibited to enhance the stability. Furthermore, it is assumed that in compound A-17, since substituents R$_1$ and R$_2$ in General Formula [1] are methyl groups and present at the para-positions of the aromatic rings, oxidation-reduction can be performed with higher stability.

Example 4

Synthesis of Compound XX-6

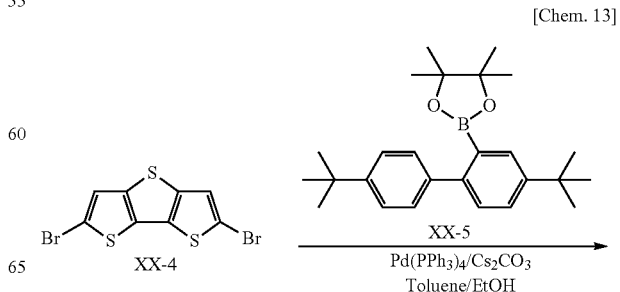

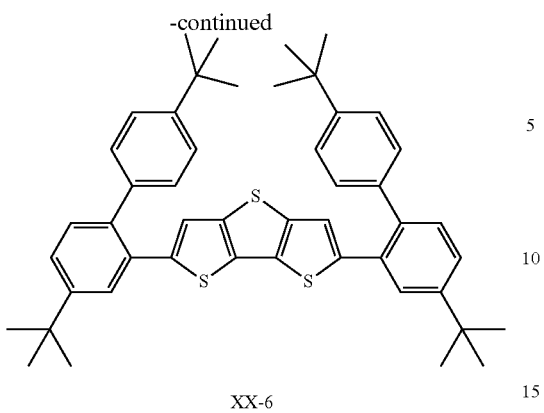

XX-6

In a 50-mL reaction container, XX-4 (177.05 mg, 0.50 mmol) and XX-5 (588.6 mg, 1.50 mmol) were mixed in a toluene/ethyl alcohol (6 mL/2 mL) mixture solvent, and dissolved oxygen was removed by nitrogen. Note that XX-5 is a compound synthesized in accordance with the procedure described in WO2005/054212. Then, Pd(PPh$_3$)$_4$ (57.8 mg, 0.05 mmol) and an aqueous solution of 2 M cesium carbonate (1.0 mL) were added to the mixture under a nitrogen atmosphere, followed by heating to 85° C. and reaction at the temperature for 17 hours. The reaction solution was cooled to room temperature, concentrated under reduced pressure, and subjected to silica gel chromatography (mobile phase: hexane/toluene=5/1) for isolation and purification to obtain XX-6 (125 mg, yield: 29%) as a white solid powder.

Mass-spectrometry (MS) and nuclear magnetic resonance spectrometry (NMR) of compound XX-6 gave the results that the molecular weight and the ratio of integrated values of NMR peaks well agreed with the structure of compound XX-6. Specifically, 724 as M$^+$ of this compound was confirmed by matrix-assisted laser desorption-ionization mass spectrometry (MALDI-MS). The measurement results of nuclear magnetic resonance spectrometry are shown below.

$^1$H-NMR (CDCl$_3$) σ (ppm): 7.56 (d, 2H), 7.43 (dd, 2H), 7.34 (s, 2H), 7.31 (s, 2H), 7.30 (s, 2H), 7.22 (s, 2H), 7.21 (s, 2H), 6.82 (s, 2H), 1.39 (s, 18H), 1.31 (s, 18H).

$^{13}$C-NMR (CDCl$_3$) σ (ppm): 150.42, 149.42, 144.63, 140.35, 138.00, 137.90, 132.64, 130.97, 130.80, 129.26, 129.06, 128.25, 127.75, 125.29, 125.11, 120.22, 34.61, 34.54, 31.40, 31.35.

The obtained compound XX-6 was dissolved in chloroform, and the absorption spectrum of this solution was measured with an ultraviolet and visible spectrophotometer as in Example 1. The maximum absorption peak, λmax, was observed at 358.5 nm in the ultraviolet region, and no absorption was observed over the entire visible light region. Thus, it was shown that the compound XX-6 was a transparent material.

Example 5 and Comparative Example 2

Durable Stability in Oxidation-Reduction Cycle

Compound A-17 obtained in Example 2, compound XX-6 obtained in Example 4, compound XX-8 obtained in Example 6, compound A-1 obtained in Example 7, and, as a comparative compound, compound XX-7 that is DTT having a t-butyl group as a substituent introduced thereinto, the steric hindrance of t-butyl group being smaller than that of the substituent of the present invention, were measured for durability against oxidation-reduction cycles. Compound XX-7 as the comparative compound was synthesized by a Friedel-Crafts reaction of t-butyl bromide (2-bromo-2-methylpropane) and DTT. The structural formula is shown below:

[Chem. 14]

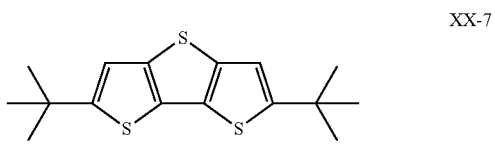

XX-7

The measurement of durability was performed using a working electrode of glassy carbon, a counter electrode of platinum, and a reference electrode of silver and dissolving each compound at a concentration of 1.0×10$^{-4}$ mol/L in a dichloromethane solution of tetrabutylammonium perchlorate (0.1 mol/L) serving as a supporting electrolyte. This solution was subjected to a repetitive square-wave potential program that is composed of oxidation at a constant potential of +1.1 V (vs. Ag/Ag+), which is not lower than the oxidation potential of the compound, for 3 seconds and reduction at a constant potential of 0 V (vs. Ag/Ag+) for 3 seconds for 20000 times. Changes in amount of oxidation peak current in CV measurement before and after the oxidation-reduction cycles for 20000 times are shown in Table 1. Herein, the "rate of change in the amount of oxidation peak current" is shown as a value obtained by adding the amount of change in current from the initial current amount being assumed as 100% to the initial current amount.

TABLE 1

| | Rate of change in the amount of oxidation peak current after 20000 times of oxidation-reduction cycles (%) |
|---|---|
| Example 2 (A-17) | 101 |
| Example 4 (XX-6) | 102 |
| Example 6 (XX-8) | 98 |
| Example 7 (A-1) | 99 |
| Comparative Example 2 (XX-7) | 81 |

In compound XX-7 of Comparative Example 2, the oxidation peak current amount was decreased after the repetition of the oxidation-reduction cycles for 20000 times, which suggested deterioration. However, in the compounds (A-17, XX-6, XX-8, and A-1) of Examples 2, 4, 6, and 7, almost no changes were observed in the oxidation current amount even after the repetition of the oxidation-reduction cycles for 20000 times. It is assumed that these results showing excellent durable stability against the oxidation-reduction cycles of the compounds of the present invention are caused by that the DTT portions of compounds A-17, XX-6, XX-8, and A-1 of the present invention are sterically protected by the bulky substituents, compared to the case of XX-7 of Comparative Example 2, and a side reaction or a deterioration reaction due to the radical cation generated by oxidation of DTT is inhibited to enhance the durable stability.

Example 6

Synthesis of Compound XX-8

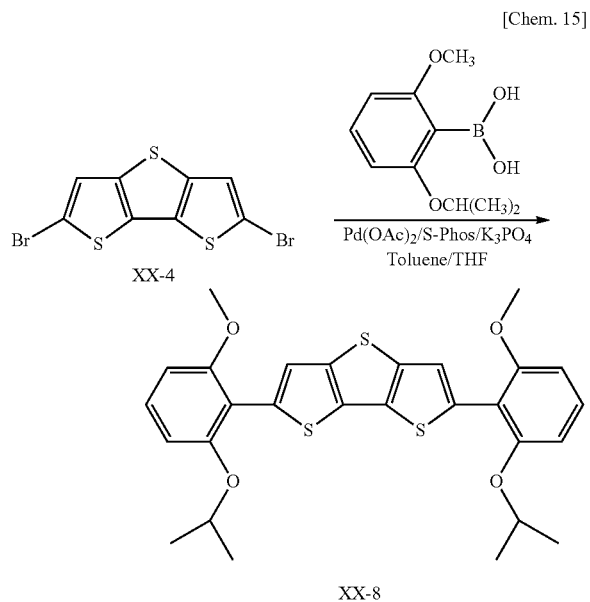

[Chem. 15]

In a 50-mL reaction container, XX-4 (177.05 mg, 0.50 mmol) and 2-isopropoxy-6-methoxyphenylboronic acid (420 mg, 2.0 mmol) were mixed in a toluene/tetrahydrofuran (6 mL/3 mL) mixture solvent, and dissolved oxygen was removed by nitrogen. Then, Pd(OAc)$_2$ (2.3 mg, 0.01 mmol), 2-dicyclohexylphosphino-2',6'-dimethoxybiphenyl (S-Phos) (10.3 mg, 0.025 mmol), and tripotassium phosphate (575.7 mg, 2.5 mmol) were added to the mixture under a nitrogen atmosphere, followed by heating to reflux at 110° C. for 8 hours. The reaction solution was cooled to room temperature, concentrated under reduced pressure, and subjected to silica gel chromatography (mobile phase: hexane/chloroform=1/2) for isolation and purification to obtain XX-8 (187 mg, yield: 71%) as a white solid powder.

Mass-spectrometry (MS) and nuclear magnetic resonance spectrometry (NMR) of compound XX-8 gave the results that the molecular weight and the ratio of integrated values of NMR peaks well agreed with the structure of compound XX-8. Specifically, 524 as M$^+$ of this compound was confirmed by matrix-assisted laser desorption-ionization mass spectrometry (MALDI-MS). The measurement results of nuclear magnetic resonance spectrometry are shown below:

$^1$H-NMR (CDCl$_3$) σ (ppm): 7.72 (s, 2H), 7.22 (t, 2H), 6.68 (d, 2H), 6.65 (d, 2H), 4.59 (m, 2H), 3.88 (s, 6H), 1.36 (s, 6H), 1.35 (s, 6H).

$^{13}$C-NMR (CDCl$_3$) σ (ppm): 157.98, 156.07, 139.80, 134.87, 131.70, 128.52, 122.26, 114.16, 107.54, 104.23, 71.62, 55.98, 22.15.

The obtained compound XX-8 was dissolved in chloroform, and the absorption spectrum of this solution was measured with an ultraviolet and visible spectrophotometer as in Example 1. The maximum absorption peak, λmax, was observed at 364.5 nm in the ultraviolet region, and no absorption was observed over the entire visible light region. Thus, it was shown that the compound XX-8 was a transparent material.

Example 7

Synthesis of Exemplary Compound A-1

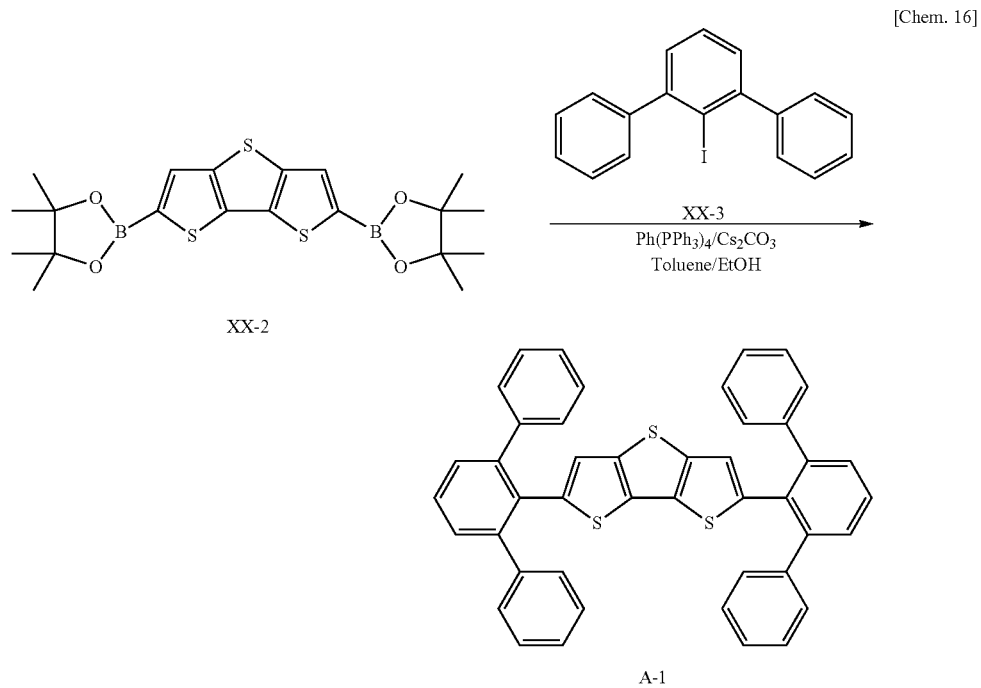

[Chem. 16]

In a 50-mL reaction container, XX-2 (526.2 mg, 1.17 mmol) synthesized in Example 1 and XX-3 (1071.2 mg, 3.0 mmol) were reacted as in Example 1 in a toluene/ethyl alcohol/tetrahydrofuran (6 mL/3 mL/8 mL) mixture solvent. The reaction solution was cooled to room temperature, concentrated under reduced pressure, and subjected to silica gel chromatography (mobile phase: hexane/chloroform=3/2) for isolation and purification to obtain A-1 (72 mg, yield: 9.4%) as a white solid powder.

Mass-spectrometry (MS) and nuclear magnetic resonance spectrometry (NMR) of compound A-1 gave the results that the molecular weight and the ratio of integrated values of NMR peaks well agreed with the structure of compound A-1. Specifically, 652 as $M^+$ of this compound was confirmed by matrix-assisted laser desorption-ionization mass spectrometry (MALDI-MS). The measurement results of nuclear magnetic resonance spectrometry are shown below:

$^1$H-NMR (THF-$d_8$) σ (ppm): 7.60 (t, 2H), 7.50 (d, 4H), 7.31-7.25 (m, 20H), 6.71 (s, 2H).

The obtained exemplary compound A-1 was dissolved in chloroform, and the absorption spectrum of this solution was measured with an ultraviolet and visible spectrophotometer as in Example 1. The maximum absorption peak, λmax, was observed at 355 nm in the ultraviolet region, and no absorption was observed over the entire visible light region. Thus, it was shown that the compound A-1 was a transparent material.

The absorption peak of oxidized exemplary compound A-1 was at 480 nm in the visible region.

Example 8

Synthesis of Compound XX-9

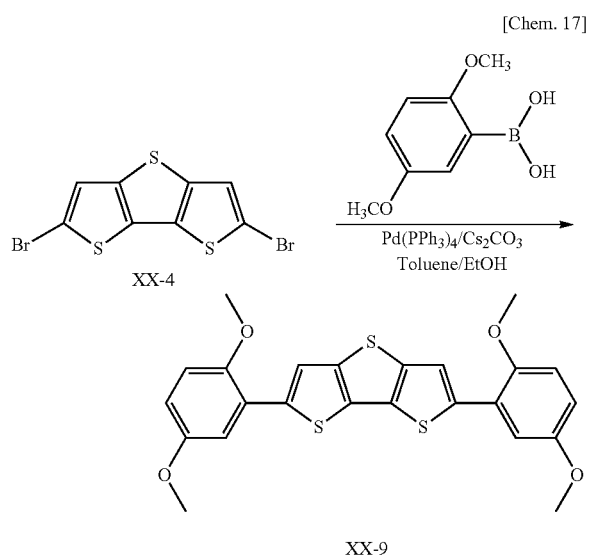

[Chem. 17]

In a 50-mL reaction container, XX-4 (176.2 mg, 0.5 mmol) and 2,5-dimethoxyphenylboronic acid (294.9 mg, 1.62 mmol) were mixed in a toluene/ethyl alcohol/tetrahydrofuran (4 mL/2 mL/4 mL) mixture solvent, and dissolved oxygen was removed by nitrogen. Then, Pd(PPh$_3$)$_4$ (57.8 mg, 0.05 mmol) and an aqueous solution of 2 M cesium carbonate (1.0 mL) were added to the mixture under a nitrogen atmosphere, followed by heating to 89° C. and reaction at the temperature for 10 hours. The reaction solution was cooled to room temperature, concentrated under reduced pressure, and subjected to silica gel chromatography (mobile phase: toluene/chloroform=1/1) for isolation and purification to obtain XX-9 (152.8 mg, yield: 65.2%) as a white solid powder.

Mass-spectrometry (MS) and nuclear magnetic resonance spectrometry (NMR) of compound XX-9 gave the results that the molecular weight and the ratio of integrated values of NMR peaks well agreed with the structure of compound XX-9. Specifically, 468 as $M^+$ of this compound was confirmed by matrix-assisted laser desorption-ionization mass spectrometry (MALDI-MS). The measurement results of nuclear magnetic resonance spectrometry are shown below:

$^1$H-NMR (CDCl$_3$) σ (ppm): 7.74 (s, 2H), 7.24 (d, 2H), 6.95 (d, 2H), 6.84 (dd, 2H), 3.94 (s, 6H), 3.84 (s, 6H).

The obtained compound XX-9 was dissolved in chloroform, and the absorption spectrum of this solution was measured with an ultraviolet and visible spectrophotometer as in Example 1. The maximum absorption peak, λmax, was observed at 390 nm in the ultraviolet region, and no absorption was observed over the entire visible light region. Thus, it was shown that the compound XX-9 was a transparent material.

As described above, the organic compounds according to the present invention are neutral and transparent and are materials having high durability against oxidation-reduction repetition. When they are used in EC devices, the EC devices are highly transparent not to show optical absorption in the visible light region when bleached and are excellent in durability and are stable.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-149481, filed Jun. 30, 2010, Japanese Patent Application No. 2011-027540, filed Feb. 10, 2011, and Japanese Patent Application No. 2011-064398, filed Mar. 23, 2011, which are hereby incorporated by reference herein in their entirety.

REFERENCE SIGNS LIST 1 dithienothiophene skeleton
2 phenyl group

The invention claimed is:
1. An organic compound represented by the following General Formula [1]:

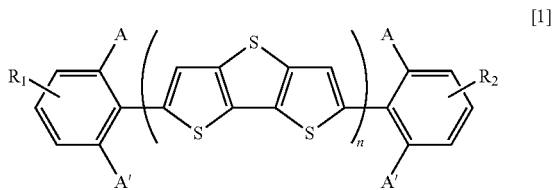

in General Formula [1], A and A' are independently selected from the group consisting of alkyl groups having 1 to 20 carbon atoms, alkoxy groups having 1 to 20 carbon atoms, and aryl groups; and the aryl groups each optionally have an alkyl group having 1 to 4 carbon atoms or an alkoxy group having 1 to 4 carbon atoms as a substituent;

R₁ and R₂ independently represent a hydrogen atom, a halogen atom, an alkyl group having 1 to 20 carbon atoms, an alkoxy group having 1 to 20 carbon atoms, an aryl group, an aralkyl group, an amino group, or a silyl group, wherein each of the aryl group, the aralkyl group, the amino group, and the silyl group optionally has an alkyl group having 1 to 4 carbon atoms as a substituent, and each of R₁ and R₂ is a substituent introduced at a meta- or para-position of a phenyl group that binds to dithienothiophene; and n represents 1 or 2.

2. The organic compound according to claim 1, wherein both A and A' are phenyl groups or methyl groups.

3. The organic compound according to claim 2, wherein both A and A' are methyl groups.

4. The organic compound according to claim 1, wherein at least one of A and A' is an alkoxy group having 1 to 20 carbon atoms.

5. The organic compound according to claim 4, wherein at least one of A and A' is an alkoxy group having 1 to 4 carbon atoms.

6. The organic compound according to claim 5, wherein at least one of A and A' is a methoxy group or an isopropoxy group.

7. An electrochromic device comprising:
a pair of electrodes; and
an electrochromic layer and an ion conductive layer disposed between the pair of electrodes, wherein
the electrochromic layer includes the organic compound according to claim 1.

8. The electrochromic device according to claim 7,
the pair of electrodes are transparent.

9. The electrochromic device according to claim 7,
the electrochromic layer is a solution layer.

10. The electrochromic device according to claim 9,
the pair of electrodes are transparent.

11. The electrochromic device according to claim 10,
the material of the pair of electrodes is selected from the group consisting of ITO, IZO, NESA, and a conductive polymer.

12. The electrochromic device according to claim 10,
wherein the electrochromic layer further comprises an electrolyte.

13. An optical filter comprising the electrochromic device according to claim 7,
wherein the pair of electrodes are transparent.

14. An optical system comprising the electrochromic device according to claim 7.

15. A camera comprising the electrochromic device according to claim 7.

* * * * *